US007938156B2

(12) United States Patent
Latos

(10) Patent No.: US 7,938,156 B2
(45) Date of Patent: May 10, 2011

(54) METHOD FOR OPTIMIZING LUMBER

(75) Inventor: Philip Latos, St. Albert (CA)

(73) Assignee: Weyerhaeuser NR Company, Federal Way, WA (US)

( * ) Notice: Subject to any disclaimer, the term of this patent is extended or adjusted under 35 U.S.C. 154(b) by 812 days.

(21) Appl. No.: 11/379,515

(22) Filed: Apr. 20, 2006

(65) Prior Publication Data

US 2007/0246125 A1    Oct. 25, 2007

(51) Int. Cl.
    *B23Q 15/00* (2006.01)
(52) U.S. Cl. .................................. 144/356; 144/357
(58) Field of Classification Search .............. 144/338,
    144/357, 363, 360, 346, 350, 351, 369; 83/13,
    83/35, 76.8, 76.7, 364, 365, 367, 368; 73/801,
    73/597, 602, 622, 73, 75, 432.1; 250/330,
    250/340, 358, 359.1, 334, 341, 563, 559.18;
    382/141, 171, 108, 110, 154, 168, 170, 173
    See application file for complete search history.

(56) References Cited

U.S. PATENT DOCUMENTS

| | | | | |
|---|---|---|---|---|
| 3,459,246 A | * | 8/1969 | Ottosson | 144/356 |
| 3,736,968 A | * | 6/1973 | Mason | 144/357 |
| 3,890,509 A | * | 6/1975 | Maxey | 250/559.25 |
| 3,931,501 A | | 1/1976 | Barr et al. | |
| 4,082,129 A | * | 4/1978 | Morelock | 144/368 |
| 4,185,672 A | * | 1/1980 | Vit et al. | 144/357 |
| 4,207,472 A | * | 6/1980 | Idelsohn et al. | 250/559.46 |
| 4,221,974 A | * | 9/1980 | Mueller et al. | 250/559.48 |
| 4,316,491 A | * | 2/1982 | Kearnes et al. | 144/357 |
| 4,774,988 A | * | 10/1988 | Washburn et al. | 144/357 |
| 4,805,679 A | * | 2/1989 | Czinner | 144/357 |
| 4,831,545 A | * | 5/1989 | Floyd et al. | 702/40 |
| 4,879,659 A | * | 11/1989 | Bowlin et al. | 700/167 |
| 4,879,752 A | * | 11/1989 | Aune et al. | 382/141 |
| 4,916,629 A | * | 4/1990 | Bogue et al. | 702/40 |
| 4,926,350 A | * | 5/1990 | Bechtel et al. | 702/36 |
| 5,097,881 A | * | 3/1992 | Mack | 144/356 |
| 5,135,597 A | * | 8/1992 | Barker | 156/264 |
| 5,421,385 A | * | 6/1995 | McGee | 144/357 |
| 5,892,808 A | * | 4/1999 | Goulding et al. | 378/63 |
| 5,915,429 A | * | 6/1999 | Pelletier et al. | 144/39 |

(Continued)

FOREIGN PATENT DOCUMENTS

CA          2406851         4/2003

(Continued)

OTHER PUBLICATIONS

McMillin, Charles W, et al ALPS—A potential new automated lumber processing system Jan. 1984 Forest Products Journal vol. 34, No. 1.*

*Primary Examiner* — Dana Ross
*Assistant Examiner* — Jennifer Chiang
(74) *Attorney, Agent, or Firm* — Rachael Vaughn

(57) ABSTRACT

Methods for optimizing lumber are provided. In an embodiment, boards cut from a log are examined for warp stability and/or knots. This occurs prior to and/or after the planing process. Based on the examination for warp stability and/or knots, the boards can be sent to a lumber upgrade process, such as for example, re-drying, edging, splitting, trimming, chopping, chipping, or the like. Accordingly, the method of the present invention enables more efficient allocation of lumber towards manufacturing needs.

20 Claims, 2 Drawing Sheets

U.S. PATENT DOCUMENTS

| | | | |
|---|---|---|---|
| 5,960,104 A * | 9/1999 | Conners et al. | 382/141 |
| 6,029,522 A * | 2/2000 | Schafer et al. | 73/598 |
| 6,062,280 A * | 5/2000 | Newnes et al. | 144/357 |
| 6,305,224 B1 * | 10/2001 | Stanish et al. | 73/597 |
| 6,358,352 B1 * | 3/2002 | Schmidt | 156/254 |
| 6,366,351 B1 * | 4/2002 | Ethier et al. | 356/237.1 |
| 6,463,402 B1 * | 10/2002 | Bennett et al. | 703/2 |
| 6,594,590 B2 * | 7/2003 | Woods et al. | 702/35 |
| 6,598,477 B2 * | 7/2003 | Floyd | 73/597 |
| 6,705,363 B2 * | 3/2004 | McGehee et al. | 144/357 |
| 6,708,122 B2 * | 3/2004 | Lessard et al. | 702/42 |
| 6,784,671 B2 * | 8/2004 | Steele et al. | 324/640 |
| 6,889,551 B2 * | 5/2005 | Andrews et al. | 73/597 |
| 6,892,614 B2 * | 5/2005 | Olsen | 83/27 |
| 6,901,352 B2 | 5/2005 | Woods et al. | |
| 6,971,423 B2 * | 12/2005 | Starr | 144/340 |
| 7,043,990 B2 * | 5/2006 | Wang et al. | 73/597 |
| 7,171,278 B2 * | 1/2007 | Baker et al. | 700/28 |
| 2003/0178586 A1 | 9/2003 | Hubert et al. | |
| 2005/0031158 A1 * | 2/2005 | Biernacki et al. | 382/100 |
| 2005/0262977 A1 | 12/2005 | Wilkerson et al. | |

FOREIGN PATENT DOCUMENTS

| | | |
|---|---|---|
| CA | 2407156 | 5/2003 |
| CA | 2581427 | 9/2007 |
| CL | 424-96 | 3/1996 |

* cited by examiner

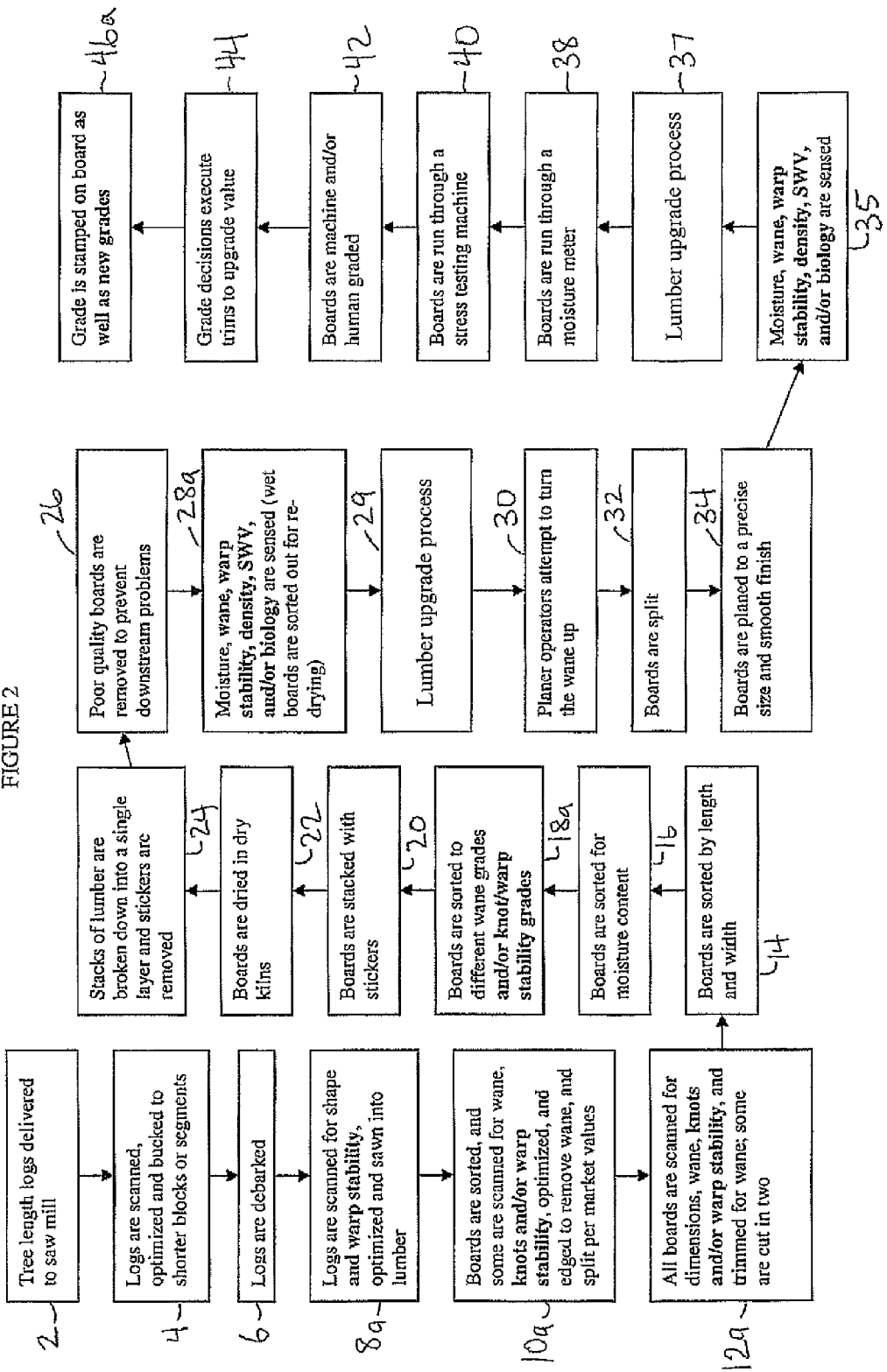

METHOD FOR OPTIMIZING LUMBER

FIELD OF THE INVENTION

This invention relates generally to a method for optimizing lumber by examining logs and boards prior to the planing process.

BACKGROUND OF THE INVENTION

Process steps for creating lumber are generally known. In a first step, tree length logs may be delivered to a saw mill. While at the saw mill, the logs may be scanned, optimized, and/or bucked to create shorter blocks or segments. The logs are also scanned for shape and sawn into lumber. The resultant boards may be sorted and scanned for wane. After further trimming, based on wane, the boards are sorted by dimensions, moisture content, and/or wane grade. The boards may then be kiln dried.

Next, the boards may be planed to a desired size and finish. The boards may then be split, tested for stress rating, and/or checked for moisture content. The boards are then graded, stamped according to their grade, and eventually packaged for shipping to a customer.

It is desirable to optimize the lumber derived from a log. Accordingly, a need exists for a method for examining logs and/or boards prior to the planing process or after the planing process to further optimize the lumber derived from the logs/boards.

BRIEF DESCRIPTION OF THE DRAWINGS

The embodiments of the present invention are described in detail below with reference to the following drawings.

FIG. 2 is a flow chart of the various steps by which lumber is derived from a log in an embodiment of the present invention.

DETAILED DESCRIPTION OF THE INVENTION

Figure 1:
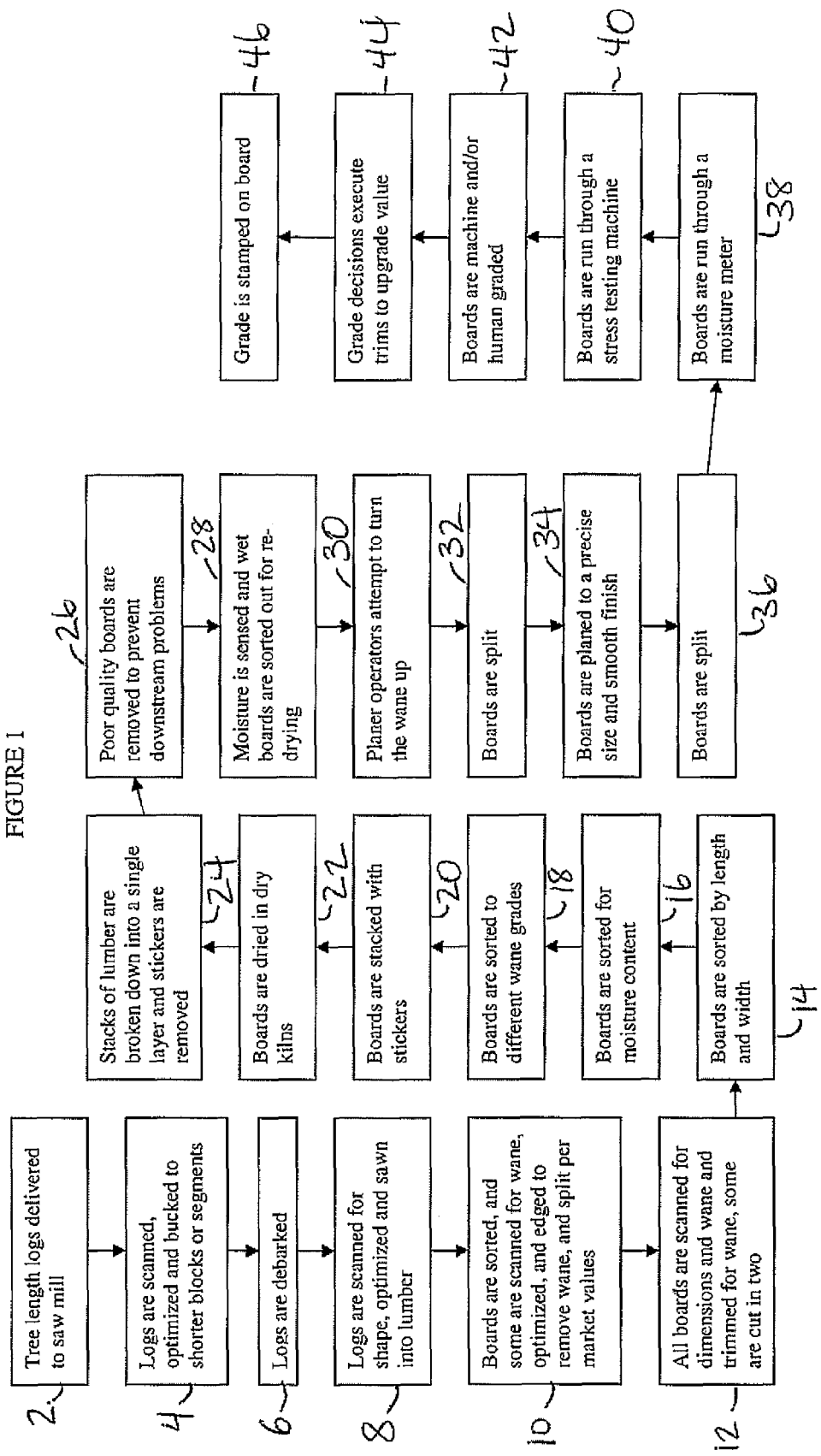
FIG. 1 is a flow chart of the various steps by which lumber is derived from a log according to known methods.

The present invention generally relates to a method for optimizing lumber. In an embodiment, boards cut from a log are examined for warp stability and/or knots. This occurs prior to the planing process and/or after planing and before grading and grade stamping. Based on the examination for warp stability and/or knots, the boards can be sent to a lumber upgrade process, such as for example, re-drying, edging, splitting, trimming, chopping, chipping, or the like. Accordingly, the method of the present invention enables more efficient allocation of lumber towards manufacturing needs.

FIG. 1 is a flow chart of the generally known processes by which lumber is derived from a log. In a first step, tree length logs may be delivered to a saw mill, as shown at step 2. While at the saw mill, the logs may be scanned, optimized, and/or bucked to create shorter blocks or segments, as shown at step 4. The logs may then be debarked, as shown at step 6. The logs are also scanned for shape, optimized and sawn into lumber, as shown at step 8. The resultant boards may be sorted and scanned for wane; they may also be optimized, edged to remove wane, or split according to market values, as shown at step 10. As shown at step 12, the boards may be scanned for dimensions and wane, and further trimmed for wane. Some of these boards may be cut into two pieces. As shown at step 14, the boards are sorted by dimensions. In some cases, the boards may also be sorted for moisture content, as shown at step 16; and/or they may be sorted by wane grade, as shown at step 18. Next, the boards are stacked with stickers, as shown at step 20. The boards may then be kiln dried, as shown at step 22. The available methods and equipment for carrying out the functions described above are well known by those skilled in the art.

Next, the boards may be sent to a planer mill. Typical equipment and processes used in a planer mill are known by those skilled in the art. While there, the stacks of lumber are broken down into a single layer and the stickers are removed, as shown at step 24. Poor quality boards are removed to prevent downstream problems, as shown at step 26. In some cases, a mill will measure moisture content of the lumber, and wet boards are sorted out for re-drying, as shown at step 28. In some embodiments, a planer operator will attempt to position a board to turn wane in an upward direction to improve grade value, as shown at step 30. In some mills, the boards are split, as shown at step 32. The boards are then planed to a desired size and finish, as shown at step 34. The boards may then be split as shown at step 36. In an embodiment, the boards are checked for moisture content, as shown at step 38. In another embodiment, the boards are tested to provide a stress rating, as shown at step 40. This may occur via, for example, a stress grading machine, such as a Linear High Grading machine, or other devices, such as a Continuous Lumber Tester. The boards are then graded, as shown at step 42. This may be performed by machine and/or human grading. Grade decisions execute trims to increase the board's grade, as shown at step 44. The boards are then stamped according to their grade, as shown at step 46, and eventually packaged for shipping to a customer.

FIG. 2 illustrates a flow chart comprising process steps of the present invention. Many of the steps illustrated in FIG. 1 are present in FIG. 2, and are numbered identically for convenience and better understanding of the invention. As seen by the figure, steps 2, 4 and 6 may be similar to known processes. Step 8*a* may differ from step 8 in that the logs may be scanned or otherwise examined for warp stability (potential methods for which will be discussed below). Likewise, step 10*a* may differ from step 10 in that boards sawn from logs may be scanned or otherwise examined for knots and/or warp stability. These boards may also be optimized and/or edged to remove wane and/or may be split per market values. Step 12*a* differs from step 12 in that the boards that are trimmed for wane, or cut in two, are scanned or otherwise examined for knots and/or warp stability. Step 18*a* differs from step 18 in that the boards are sorted according to knot properties and/or warp stability in addition to wane grades.

At step 28*a* boards may be examined for wane, warp stability, density, stress wave velocity, and/or biology in addition to moisture measurement. At step 29, the boards may be sent to the lumber upgrade process based on the examined properties in step 28*a*. These upgrade processes may be, for example, re-drying, edging, splitting, trimming, chopping, chipping, or the like. The intent of this scanning and preprocessing is to sort boards towards the appropriate manufacturing process and/or to upgrade a board for the planing process. For example, the method may involve upgrading wet boards by microwave redrying; passing those wide boards that have the greatest value as wides through the lumber process; splitting those wide boards to become narrow boards if the board quality allows more value in a narrow boards; edging those boards that could be upgraded by removing wane; or trimming or chopping a board before planing to get more value for the rough trim blocks than planed trim blocks. The warp stability and/or knot property examination may allow additional grades to be assigned to the boards respective of these characteristics, as shown at step 46*a*; prior to packaging and transport to a customer.

In an embodiment, the boards may be examined after being planed, as shown at step 35. More specifically, the examination may be for moisture, wane, warp, stability, density, stress wave velocity, biology, or the like. The boards may then be sent for an upgrade process, similar to those described above, as shown at step 37. In this embodiment, it is contemplated that the boards could be examined both before and after the planing process. In an embodiment, part of the examination of the board may be done before the planing process and part of the examining process may be done afterwards. In this embodiment, it is contemplated that only certain properties are examined prior to planing, and other properties are examined after planing. In other embodiments, the boards may be examined either before or after the planing process. Further, logs may or may not be examined for warp stability and/or knot properties prior to being sawn for lumber.

The methods for determining warp stability or any of the other properties mentioned above may involve the use of single and/or multiple sensor group systems to provide qualitative and/or quantitative estimates. It has been discovered that estimates of warp/dimensional stability can be much improved when an assortment of measurements are used together, where each measurement contributes information relating to one or more variables. The measurements may be taken at one or more sections of the wood product (i.e., log or board), which may differ in size given a particular embodiment. The properties observed at the one or more sections may allow a qualitative and/or quantitative estimate of dimensional stability of a region of interest. In a first embodiment, the region of interest may be a coupon or other portion of the wood product. In another embodiment, the region of interest may overlap with one or more sections of the wood product. In another embodiment, the region of interest may be the entire wood product. In yet another embodiment, the region of interest may be the same as the one or more sections detected by the sensor group(s). In another embodiment, the region of interest does not have an overlap with the one or more sections. The dimensional stability assessed may be cup, crook, bow, twist, length stability, thickness stability, width stability, or any combination of these.

In an embodiment of the present invention, a classification algorithm may be created to classify a wood product into one of a plurality of groups or categories. The groups may be based on qualitative or quantitative characteristics. For example, in an embodiment, the categories may be different grades. Warp classification of wood products, such as boards may require inputs from one or more sensor groups detecting properties of the boards. The sensor groups may be a part of those systems previously mentioned for analyzing a wood product. The technologies for these systems are known by those skilled in the art. For example, the sensor groups may obtain moisture content measurement, electrical property measurement, structural property measurement, acousto-ultrasonic property measurement, light scatter (tracheid-effect) measurement, grain angle measurement, shape measurement, color measurement, spectral measurement and/or defect maps. Structural property measurement may measure modulus of elasticity, density, specific gravity, strength, or a combination of these. Acousto-ultrasonic property measurement measures may measure velocity and/or damping. The spectral measurement may be characterized by absorption or reflectance values over a wavelength spectrum ranging from ultraviolet through near infrared.

Using this approach, the prediction model or algorithm of the present invention may use inputs of many different resolution scales. Some examples are board average MOE, moisture content measured across the width of the board in one foot increments along the length of the board, spectroscopy data collected every inch, or laser data collected every ¼ inch.

The inputs are functions of the sensor signals and may be either quantitative or qualitative. For example, an input could be the estimated moisture content for each 12 inch lineal section of a piece of lumber, as estimated by a moisture meter. Another example is an indicator for the presence or absence of a knot in a 12 inch by 1 inch section of wood, based oil a color image. Inputs may be direct sensor measurements, pre-processed signals, combined signals from several sensors or predicted measures from other sensors. Signal pre-processing may include, but is not limited to, such steps as filtering, smoothing, derivative calculations, power spectrum calculations, Fourier transforms, etc., as is well known in the art. Predicted measurements from other sensors may include, but are not limited to, shrinkage-coefficients predicted from sensors which measure the light scattering and light absorption properties of wood and used as inputs to a partial least squares, or "PLS", prediction model.

The prediction algorithm(s) or model(s) based on the set of inputs can be derived using many techniques which include, but are not limited to, regression trees, classification trees, linear discriminant analysis, quadratic discriminant analysis, logistic regression, Partial Least Squares or other supervised learning techniques such as neural networks. There are many forms of equations or algorithms that could be used, and a general reference is Hastie, et al[1].

[1] Hastie, T., Tibshirani, R., and Friedman, J., (2001) The Elements of Statistical Learning, Springer, N.Y.

These algorithms can be developed to classify boards into 2 or more groups. For example, boards might be classified into four grades (#1 grade, #2 grade, #3 grade, #4 grade) or into two classifications like warp stable and warp unstable, or into three categories like crook less than 0.25 inches, crook between 0.25 and 0.5 inches, crook greater than 0.5 inches. Typically, the parameters in the models or algorithms are derived from a training-set of data and the performance is tested on a testing-set of data before being used in production, although other approaches exist.

Various embodiments are contemplated involving the use of sensor groups and algorithms. In a first embodiment, a single sensor group may provide inputs to a classification algorithm which classifies wood products into one of a plurality of groups or categories, such as grades, for example.

In a second embodiment, a single sensor group may provide inputs to a classification algorithm as in the previous example. However, in this embodiment, a second algorithm may be selected after classifying the wood product. This second algorithm may be selected from a plurality of algorithms which are used to assess the dimensional stability in a quantitative manner.

In a third embodiment, two or more sensor groups may provide two or more inputs to a classification algorithm to classify wood products into one of a plurality of categories.

In a fourth embodiment, two or more sensor groups may provide two or more inputs to an algorithm for providing a quantitative assessment of dimensional stability of wood products.

In a fifth embodiment, two or more sensor groups may provide two or more inputs to a classification algorithm to classify wood products into one of a plurality of categories. Next, a second algorithm may be selected after classifying the wood product. This second algorithm may be selected from a plurality of algorithms which are used to assess the dimensional stability in a quantitative manner.

Other methods for determining warp stability, wane, moisture, knot properties, or the like for a log or board are contemplated, including those described in U.S. Pat. Nos. 6,308,571; 6,305,224; and 6,293,152 to Stanish et al., or any other known methods currently used at mill sites. These methods could be implemented into the process steps described above.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for optimizing lumber derived from a log, the method comprising the steps of:
    debarking the log;
    scanning the log to determine a first warp stability prior to cutting the log;
    cutting the log to provide a plurality of boards, wherein cutting the log is optimized based on the first warp stability;
    scanning the plurality of boards to determine a second warp stability and/or wane for each of the plurality of boards;
    selecting a lumber upgrade process for each of the boards, wherein selecting the lumber upgrade process for each of the boards is optimized based on the second warp stability for each of the plurality of boards; and
    planing one or more of the plurality of boards after the board is subjected to the lumber upgrade process;
    wherein the first warp stability and the second warp stability are determined by inputting qualitative and/or quantitative characteristics measured by scanning sensors into prediction algorithms.

2. The method of claim 1 wherein the lumber upgrade process is edging of the board.

3. The method of claim 1 wherein the lumber upgrade process is splitting of the board.

4. The method of claim 1 wherein the lumber upgrade process is trimming of the board.

5. The method of claim 1 wherein the lumber upgrade process is chipping of the board.

6. The method of claim 1 wherein the plurality of boards are also examined for knot properties prior to planing.

7. The method of claim 6 wherein the lumber upgrade process selected is also based on the knot properties.

8. The method of claim 1 further comprising the step of:
    assigning a grade to one or more of the boards wherein the grade is based on one or more of the following: moisture content, wane, warp stability, density, stress wave velocity measurements and biology.

9. A method for optimizing lumber derived from a log, the method comprising the steps of:
    debarking the log;
    scanning the log to determine a first warp stability prior to cutting the log;
    cutting the log to provide a plurality of boards, wherein cutting is optimized based based on the first warp stability;
    scanning the plurality of boards to determine a second warp stability and/or wane for each of the plurality of boards;
    sorting each of the boards based on the second warp stability;
    selecting a lumber upgrade process for each of the boards based on the second warp stability, wherein selecting the lumber upgrade process is optimized based on the second warp stability;
    planing one or more of the plurality of boards after the board is subjected to the lumber upgrade process;
    scanning one or more of the plurality of boards to determine a third warp stability after the board is planed; and
    assigning a grade to one or more of the boards based on the third warp stability;
    wherein the first warp stability, the second warp stability, and the third warp stability are determined by inputting qualitative and/or quantitative characteristics measured by scanning sensors into prediction algorithms.

10. The method of claim 9 wherein the lumber upgrade process is edging of the board.

11. The method of claim 9 wherein the lumber upgrade process is splitting of the board.

12. The method of claim 9 wherein the lumber upgrade process is trimming of the board.

13. The method of claim 9 wherein the lumber upgrade process is chipping of the board.

14. The method of claim 9 wherein the plurality of boards are also examined for knot properties prior to planing.

15. The method of claim 9 wherein the lumber upgrade process selected is also based on the knot properties.

16. A method for optimizing lumber derived from a log, the method comprising the steps of:
    debarking the log;
    scanning the log to determine a first warp stability;
    cutting the log to provide a plurality of boards, wherein cutting the log is optimized based on the first warp stability;
    examining the plurality of boards to determine a second warp stability and/or wane for each of the plurality of boards;
    sorting each of the boards into at least two groups of boards based on the second warp stability;
    edging each of the boards in at least one of the at least two groups to remove wane;
    splitting each of the boards in at least one of the at least two groups according to market values;
    examining each of the boards in the at least two groups to determine a third warp stability;
    trimming at least a portion of the boards in the at least two groups based on the third warp stability;
    examining each of the boards in the at least two groups to determine a fourth warp stability; and
    re-sorting the boards in the at least two groups for re-drying;
    wherein the first warp stability, the second warp stability, the third warp stability, and the fourth warp stability are determined by inputting qualitative and/or quantitative characteristics measured by scanning sensors into prediction algorithms.

17. The method of claim 16 wherein the step of examining the log further comprises scanning the log to determine shape.

18. The method of claim 16 wherein the step of examining the plurality of boards further comprises scanning for wane and knots.

19. The method of claim 16 wherein the step of examining each of the boards in the at least two groups to determine the third warp stability further comprises scanning for wane and knots.

20. The method of claim 16 wherein the step of examining each of the boards in the at least two groups to determine the fourth warp stability further comprises scanning for wane and knots.

* * * * *